(12) United States Patent
Shani et al.

(10) Patent No.: US 8,714,181 B2
(45) Date of Patent: *May 6, 2014

(54) IRRIGATION CONTROL SYSTEM

(75) Inventors: Uri Shani, Nes-Ziona (IL); Abraham Schweitzer, D.N. Negev (IL)

(73) Assignees: Netafim, Ltd., Tel Aviv (IL); Yissum Research Development Company of the Hebrew University of Jerusalem, Givat Ram (IL)

( * ) Notice: Subject to any disclaimer, the term of this patent is extended or adjusted under 35 U.S.C. 154(b) by 237 days.

This patent is subject to a terminal disclaimer.

(21) Appl. No.: 13/240,815

(22) Filed: Sep. 22, 2011

(65) Prior Publication Data

US 2012/0006421 A1    Jan. 12, 2012

Related U.S. Application Data

(62) Division of application No. 12/193,054, filed on Aug. 18, 2008, now Pat. No. 8,051,871.

(60) Provisional application No. 60/935,571, filed on Aug. 20, 2007.

(51) Int. Cl.
*A01G 25/00* (2006.01)

(52) U.S. Cl.
USPC .......... 137/78.3; 73/73; 47/48.5; 239/63

(58) Field of Classification Search
USPC ............ 137/78.2, 78.3; 239/63; 47/48.5; 73/826, 862.391, 837, 807, 816, 825, 73/823, 857
See application file for complete search history.

(56) References Cited

U.S. PATENT DOCUMENTS

| | | | |
|---|---|---|---|
| 3,898,872 A | 8/1975 | Skaling et al. |
| 4,068,525 A | 1/1978 | Skaling |
| 4,548,225 A | 10/1985 | Busalacchi |
| 5,113,888 A | 5/1992 | Beggs |
| 5,156,179 A | 10/1992 | Peterson et al. |
| 5,273,066 A | 12/1993 | Graham et al. |
| 6,314,340 B1 | 11/2001 | Mecham et al. |
| 6,712,552 B1 | 3/2004 | Kepler et al. |
| 6,782,909 B1 | 8/2004 | Ragless |
| 6,978,794 B2 | 12/2005 | Dukes et al. |
| 7,631,545 B2 | 12/2009 | Skaling et al. |

*Primary Examiner* — Craig Schneider
(74) *Attorney, Agent, or Firm* — Womble Carlyle (57) ABSTRACT

A tensiometer for use in determining matric potential of a soil includes a water inlet; a hydraulic coupler comprising a porous material for providing hydraulic coupling between water that enters the inlet and the soil; and a septum that seals water that enters the inlet against ingress of air via the porous material.

29 Claims, 10 Drawing Sheets

IRRIGATION CONTROL SYSTEM

RELATED APPLICATIONS

The present application is a Divisional of U.S. patent application Ser. No. 12/193,054, filed Aug. 18, 2008, now U.S. Pat. No. 8,051,871, which claims the benefit under 35 U.S.C. 119(e) of U.S. Provisional Application 60/935,571 filed Aug. 20, 2007. The contents of the aforementioned applications are incorporated by reference in their entirety.

FIELD

The invention relates to systems and apparatus for controlling irrigation systems.

BACKGROUND OF THE INVENTION

Irrigation systems that deliver water, often containing plant nutrients, pesticides and/or medications, to plants via networks of irrigation pipes are very well known. In some irrigation systems, external sprinklers, emitters or drippers, are connected to the irrigation pipes to divert water from the pipes and deliver the water to plants. In many such irrigation networks, water from the pipes is delivered to the plants by emitters or drippers that are installed on or "integrated" inside the irrigation pipes. For convenience, any of the various types of devices used in an irrigation system to divert water from an irrigation pipe in the system and deliver the diverted water to the plants is generically referred to as an emitter. Spacing between emitters, and emitter characteristics are often configured to respond to different irrigation needs of plants that the irrigation system is used to irrigate.

For a given configuration of irrigation pipes and emitters, quantities of water delivered by the irrigation system may be controlled by controlling any of various water flow control devices, such as water pumps, flow valves and check valves, and/or combinations of flow control devices known in the art. Flow control devices may operate to control water from a source that provides water to all of, or a portion of, irrigation pipes in an irrigation system or to control water from individual emitters in the irrigation system.

Israel Patent Application 177552 entitled "Irrigation Pipe" filed Aug. 17, 2006, the disclosure of which is incorporated herein by reference, describes an irrigation system having irrigation pipes comprising integrated emitters having different pressure thresholds at which they open to deliver water from the pipes. Which emitters open to deliver water, is controlled by changing pressure in the irrigation pipes. U.S. Pat. No. 5,113,888, "Pneumatic Moisture Sensitive Valve", the disclosure of which is incorporated herein by reference, describes a spray device having its own valve that is opened and closed to control amounts of water that the device sprays on plants.

Various automatic and/or manual methods and systems are used to determine when and how much water to supply to plants irrigated by an irrigation system and to control water flow devices in the system accordingly. U.S. Pat. No. 5,113,888 noted above, controls the water flow valve in the spray device described in the patent responsive to soil moisture. The spray device comprises an element located in the soil that has pores, which are blocked when soil water moisture is above a predetermined amount and that are open when soil moisture is below a predetermined amount. When the pores are open, air is released from a chamber in the valve relieving pressure that keeps the flow valve closed to allow the valve to open and water to flow to and be sprayed from the spray device. U.S. Pat. No. 6,978,794, the disclosure of which is incorporated herein by reference, describes controlling an irrigation system responsive to soil moisture determined by at least one time domain reflectometry sensor ("TDRS") located in the soil. The patent describes using multiple TDRS's at a different soil depth to provide measurements of soil moisture content. U.S. Pat. No. 6,314,340, the disclosure of which is incorporated herein by reference, describes controlling water responsive to diurnal high and low temperatures.

For many agricultural and scientific applications, soil water matric potential is used as a measure of soil moisture content and suitability of soil conditions for plant growth and irrigation systems are often controlled responsive to measurements of soil matric potential. Water matric potential, conventionally represented by "$\psi$", is a measure of how strongly particulate soil matter attracts water to adhere to the particulate surfaces. The drier a soil, the stronger are the forces with which soil particles attract and hold water to their surfaces and the greater is the water matric potential. As matric potential of a soil increases, the more difficult it is for plants to extract water from the soil. When soil gets so dry that plants cannot extract water from the soil, plant transpiration stops and plants wilt.

Matric potential has units of pressure, is typically negative, and is conventionally measured using a tensiometer. A tensiometer usually comprises a porous material that is connected by an airtight seal to a sealed reservoir filled with water. The porous material is placed in contact with soil whose matric potential, and thereby moisture content, is to be determined and functions to couple the reservoir to the soil to allow water but not air to pass between the reservoir and soil. The forces that attract water to soil particles draw water through the porous material from the reservoir and generate a vacuum in the reservoir. The drier the soil, the greater are the forces that draw water from the reservoir through the porous material and the greater is the vacuum, i.e. the pressure of the vacuum decreases. As soil moisture increases, the forces that attract water to the soil particles decrease and water is drawn from the soil through the porous material into the reservoir and pressure of the vacuum increases. The vacuum increases (pressure decreases) or decreases (pressure increases) as water content of the soil respectively decreases or increases. A suitable pressure monitor is used to determine pressure of the vacuum and thereby provide a measure of the soil matric potential.

The porous material in a tensiometer is usually a ceramic and is often formed having a cuplike or test tube-like shape. However, U.S. Pat. No. 4,068,525, the disclosure of which is incorporated herein by reference, notes that the porous material "may be formed from any of a wide variety of materials, including ceramics, the only requirement being that the 'bubbling pressure', the pressure below which air will not pass through the wettened pores of the material, must be greater than normal atmospheric pressure, to prevent bubbles of air from entering the instrument". It is noted that bubbling pressure is generally maintained only when the porous material is saturated with water.

Additionally, the porous material should provide good hydraulic contact between the soils and the water reservoir. The latter constraint with respect to soil contact generally requires that the porous material be in relatively intimate mechanical contact with soil particles. Whereas such contact can usually be provided by a surface of a ceramic, for coarse soils or gravels, such mechanical and resulting hydraulic contact can be difficult to obtain using a ceramic material. Gee et al, in an article entitled "A Wick Tensiometer to Measure Low Tensions in Coarse Soils"; Soil Sci. Soc. Am. J.

54:1498-1500 (1990) describes a tensiometer for use in coarse soils in which the porous material "is constructed from paper toweling or other comparable wicking material rolled tightly into a cylinder (.about.0.7 cm in diameter and .about.7 cm long)." The authors note that the tightly rolled wicking material when wetted was pressure tested for suitable bubbling pressure.

U.S. Pat. No. 5,156,179, the disclosure of which is incorporated herein by reference, describes an irrigation system that is controlled using a tensiometer responsive to water matric potential. The system comprises a "flow controller device" that includes a valve assembly connected with the tensiometer to "provide automatic control of flow of water for irrigation". Changes in pressure in the tensiometer move a piston in the valve to provide "variable control of the rate of flow" through the valve assembly "according to the matric tension of the soil for water".

SUMMARY OF THE INVENTION

An aspect of some embodiments of the invention relates to providing a tensiometer for measuring matric potential of a soil, for which functions of providing hydraulic contact with the soil and sealing a water reservoir used with or comprised in the tensiometer against ingress of air through the hydraulic contact are provided by different components of the tensiometer.

According to an aspect of some embodiments of the invention, a septum, hereinafter a "sealing septum" interfaces the tensiometer water reservoir with a component of the tensiometer formed from a porous material that provides hydraulic contact between the tensiometer reservoir and the soil and when wet substantially seals the reservoir against ingress of air through the porous material. For convenience of presentation, the component formed from the porous material is referred to as a "hydraulic coupler".

In an embodiment of the invention, because the sealing septum substantially provides appropriate sealing of the water reservoir, the porous material of the hydraulic coupler is generally not required when wet to have a bubbling pressure greater than an absolute value of a minimum matric potential of the soil in which the tensiometer is to be used. (As noted above, matric potential is usually a negative pressure, and a minimum matric potential is negative pressure having a greatest absolute value. Bubbling pressure of a material is the negative of a minimum matric potential at which air will not pass through the material, generally when the material is properly wetted.) By substantially separating the function of providing hydraulic contact with a soil and the function of sealing against passage of air, a relatively broad spectrum of materials can be used for the hydraulic coupler and a tensiometer can advantageously be configured for specific agricultural applications while also providing relatively improved hydraulic contact with the soil.

For example, according to an aspect of some embodiments of the invention, the hydraulic coupler comprises a porous material in which plant roots are able relatively easily to grow. Optionally, the porous material comprises a woven and/or non-woven geotextile and/or fiberglass. Practice of the invention is not however, limited to such materials and a tensiometer in accordance with an embodiment of the invention may, for example, comprise any hydrophilic material characterized by suitable porosity and may of course comprise relatively rigid materials such as ceramics.

It is noted that the roots of many plants are able to generate hydraulic pressure equivalent to about 15 atmospheres in order to extract water from soil. Such pressure can cause relatively steep gradients in soil moisture for which soil in a near neighborhood of a plant's roots is substantially drier than soil outside of the near neighborhood. Since plant growth and health are generally relatively sensitive to the soil environment near to their roots, a tensiometer for which plant roots are able to grow inside the tensiometer's hydraulic coupler can provide water matric potential measurements advantageously sensitive to soil conditions in the near neighborhoods of plant roots. Such measurements can be particularly advantageous for use in controlling an irrigation system that provides water to the plants.

An aspect of some embodiments of the invention relates to providing a tensiometer that is relatively inexpensive and simple to make and use.

In an embodiment of the invention, a tensiometer comprises a housing having a first housing part formed having an inlet orifice for communication with a sealed water reservoir and a second housing part formed to mate with the first part. The mated parts are assembled sandwiching a sealing septum between the orifice and a first region of a porous hydraulic coupling material that is located in the tensiometer housing when the tensiometer is assembled. A second region of the hydraulic coupling material is located outside of the assembled housing and provides hydraulic coupling of the tensiometer to soil for which the tensiometer provides matric potential measurements. Optionally the first and second housing parts are formed by injection molding plastic. Optionally, the sealing septum is formed from materials readily available in the market such as a plastic, ceramic, or sintered metal characterized by a porosity having suitable uniformity and pore size. Optionally, the pore size has a characteristic dimension having an average between about 0.5 micron and about 1 micron. Optionally, the hydraulic coupling material comprises a geotextile. The tensiometer may rapidly be assembled by any of various methods known in the art, such as by ultrasonic welding, gluing, or snap locking the first and second housing parts together.

An aspect of some embodiments of the invention, relates to providing a configuration of tensiometers that provides a measurement of water matric potential responsive to water matric potential conditions over a relatively large area.

According to an aspect of some embodiments of the invention, a plurality of tensiometers is distributed over the area and the tensiometers in the plurality are coupled to a same common water reservoir. Pressure of a partial vacuum in the common reservoir is responsive to the water matric potential at each of the locations at which a tensiometer of the plurality of tensiometers is located. At equilibrium, pressure of a partial vacuum in the common water reservoir provides a measure, hereinafter a "representative matric potential", of water matric potential in the area that is intermediate a highest and lowest value for water matric potential provided by the tensiometers. A suitable pressure or vacuum gauge is used to provide a measurement of pressure in the reservoir and thereby a measure of the representative matric potential.

An aspect of some embodiments of the invention relates to providing an improved water management algorithm for controlling irrigation of a field responsive to water matric potential.

In an embodiment of the invention, an irrigation cycle defined by the algorithm comprises a period of active irrigation during which the algorithm controls an irrigation system to provide pulses of water to a field responsive to measurements of water matric potential in the field. Optionally, the cycle is a diurnal cycle. Optionally pulses of water are provided responsive to comparing measurements of water matric potential to a calibration water matric potential measurement.

In an embodiment of the invention, the calibration water potential measurement is acquired prior to the active irrigation period at a time for which plants in the field have a relatively small demand for water. Generally, plants exhibit a minimum in water demand at night, often in the early dawn hours and it is at such hours that calibration matric potential measurements are, optionally, acquired. Optionally, the water matric potential measurements are acquired using a tensiometer.

In an embodiment of the invention, an algorithm controls an irrigation system to provide water to a field continuously during an active irrigation period. The duration of the active irrigation period is determined by the algorithm responsive to a comparison of a measurement of water matric potential for the field with a calibration water matric potential.

There is therefore provided in accordance with an embodiment of the invention, a tensiometer for use in determining matric potential of a soil comprising: a water inlet; a hydraulic coupler comprising a porous material for providing hydraulic coupling between water that enters the inlet and the soil; and a septum that seals water that enters the inlet against ingress of air via the porous material. Optionally, the porous material comprises a geotextile. Additionally or alternatively, the porous material is adapted to enable growth of plant roots therein.

In some embodiments of the invention, the septum comprises a septum surface, at least a part of which is contiguous with water that enters the inlet. Optionally, the tensiometer comprises a water labyrinth having baffles. Optionally, a portion of the septum surface contacts the baffles.

In some embodiments of the invention, the septum comprises a membrane and the septum surface is a surface of the membrane. Optionally, the membrane comprises a plurality of layers. Optionally, the layers comprise a first layer having a bubbling pressure greater than about a maximum absolute value of the matric potential of the soil in which the tensiometer is used. Optionally, the first layer is supported by at least one support layer. Optionally, the first layer is sandwiched between two support layers.

In some embodiments of the invention, the septum has a bubbling pressure greater than about a maximum absolute value of the matric potential of the soil in which the tensiometer is used.

In some embodiments of the invention, the bubbling pressure is about equal to one atmosphere.

In some embodiments of the invention, a tensiometer comprises an elastic member that resiliently presses the porous material to the septum.

In some embodiments of the invention, a tensiometer comprises a water reservoir coupled to the water inlet.

In some embodiments of the invention, a tensiometer comprises a device for providing a measure of pressure in the water reservoir.

There is further provided in accordance with an embodiment of the invention, an irrigation system comprising: an irrigation pipe having at least one output orifice for outputting water from the pipe; at least one tensiometer according to an embodiment of the invention coupled to the irrigation pipe so that water output from an orifice of the at least one orifice is constrained to pass substantially directly from the orifice through the hydraulic coupler. Optionally, the irrigation pipe comprises at least one emitter and an output orifice is an orifice of the at least one emitter. Additionally or alternatively, the at least one emitter is an integrated emitter. Additionally or alternatively, the at least one emitter comprises a plurality of emitters.

In some embodiments of the invention, each of the at least one tensiometer is coupled to a same water reservoir.

There is further provided in accordance with an embodiment of the invention, apparatus for use in determining matric potential of a soil comprising: a plurality of tensiometers; and a same water reservoir to which all the tensiometers are hydraulically coupled. Optionally, the plurality of tensiometers comprises a tensiometer in accordance with an embodiment of the invention. Additionally or alternatively, the apparatus comprises a valve adapted to connect the irrigation system to a water source and operable to enable water from the water source to enter the reservoir and remove air therefrom.

There is further provided in accordance with an embodiment of the invention, an irrigation system comprising: an irrigation pipe having at least one output orifice for outputting water from the pipe; at least one tensiometer comprising a hydraulic coupler for coupling the tensiometer to soil irrigated by the irrigation system; and a valve adapted to connect the irrigation system to a water source and operable to enable water from the water source to enter the at least one tensiometer and flush air from the tensiometer and coupler.

There is further provided in accordance with an embodiment of the invention, a tensiometer for use in determining matric potential of a soil comprising: a water inlet; a hydraulic coupler comprising a porous material for providing hydraulic coupling between water that enters the inlet and the soil; a valve adapted to connect the tensiometer to a water source and operable to enable water from the water source to enter the tensiometer and flush the hydraulic coupler.

There is further provided in accordance with an embodiment of the invention, a method of irrigating a field, the method comprising: acquiring a calibration water matric potential for the field; and irrigating the field with an amount of water responsive to the value of the calibration matric potential. Optionally, irrigating a field comprises performing an irrigation cyclically. Optionally, irrigating the field cyclically comprises irrigating the field in diurnal cycles. Optionally, acquiring a calibration water matric potential comprises acquiring a calibration water matric potential at least once a day.

In some embodiments of the invention, the field comprises plants and acquiring the calibration water matric potential comprises acquiring the matric potential when the plants exhibit relatively small water demand.

In some embodiments of the invention, providing an amount of water comprises providing a pulse of water. Optionally, providing an amount of water comprises acquiring a water matric potential measurement for the field in addition to the calibration water matric potential, comparing the additional water matric potential measurement to the calibration water matric potential, and providing an amount of water responsive to the comparison. Optionally, comparing the additional water matric to the calibration matric potential comprises determining their difference. Optionally, providing a pulse of water comprises providing the pulse responsive to the difference.

In some embodiments of the invention, providing water comprises providing water continuously. Optionally, providing water continuously, comprises determining an irrigation period responsive to the calibration water matric potential and providing water continuously for the determined irrigation period. Optionally, determining the irrigation period comprises determining the irrigation period responsive to a difference between the calibration water matric and a previously determined calibration water matric.

There is further provided in accordance with an embodiment of the invention, an irrigation system comprising: an irrigation pipe having at least one output orifice for outputting liquid from the pipe; at least one hydraulic coupler coupled to the irrigation pipe so that liquid output from an orifice of the at least one orifice passes through the hydraulic coupler; and at least one sensing means coupled to the hydraulic coupler to sense a property associated with liquid in the hydraulic coupler, responsive to which property output of water via the at least one orifice is controlled. Optionally, the sensed property comprises matric potential. Additionally or alternatively, the sensed property comprises moisture content of the hydraulic coupler.

Optionally, the irrigation system comprises a controller that controls output of water via the at least one orifice responsive to the sensed property.

BRIEF DESCRIPTION OF FIGURES

Non-limiting examples of embodiments of the invention are described below with reference to figures attached hereto and listed below. Identical structures, elements or parts that appear in more than one figure are generally labeled with a same numeral in all the figures in which they appear. Dimensions of components and features shown in the figures are chosen for convenience and clarity of presentation and are not necessarily shown to scale.

DETAILED DESCRIPTION

Figure 1A:
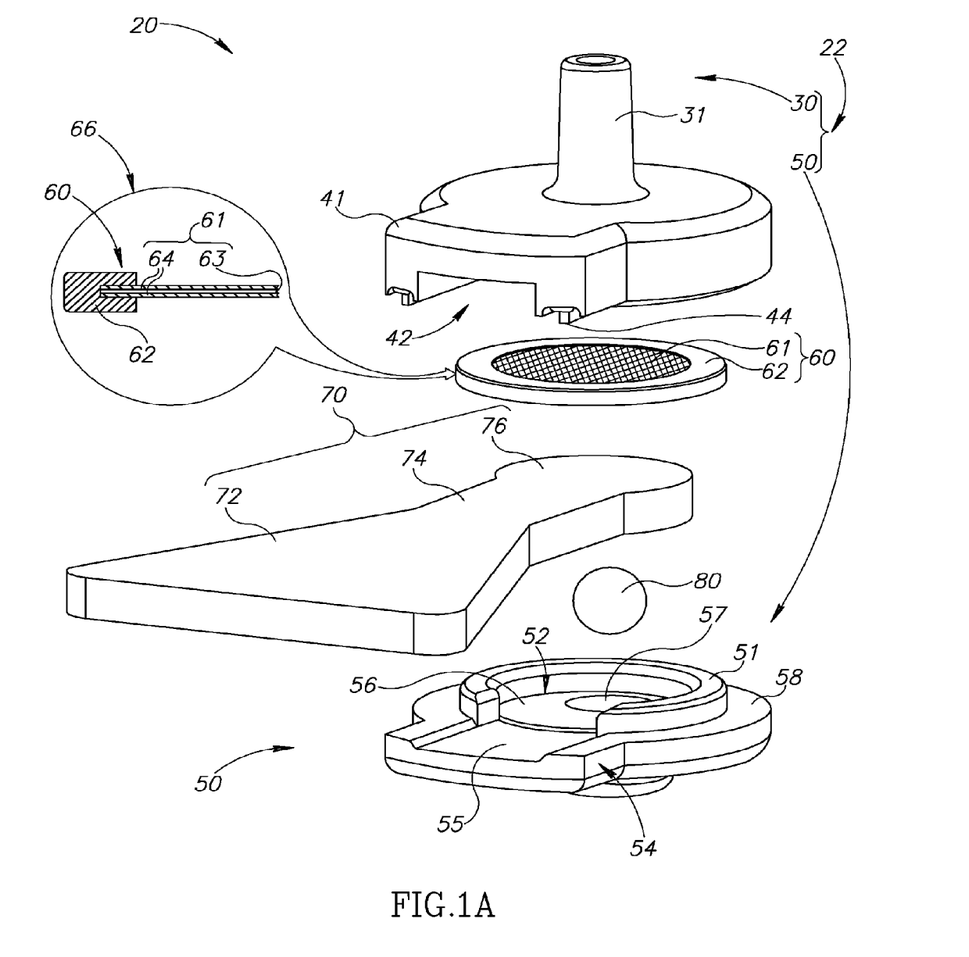
FIG. 1A schematically shows an exploded view of a tensiometer, in accordance with an embodiment of the invention.
Figure 1B:
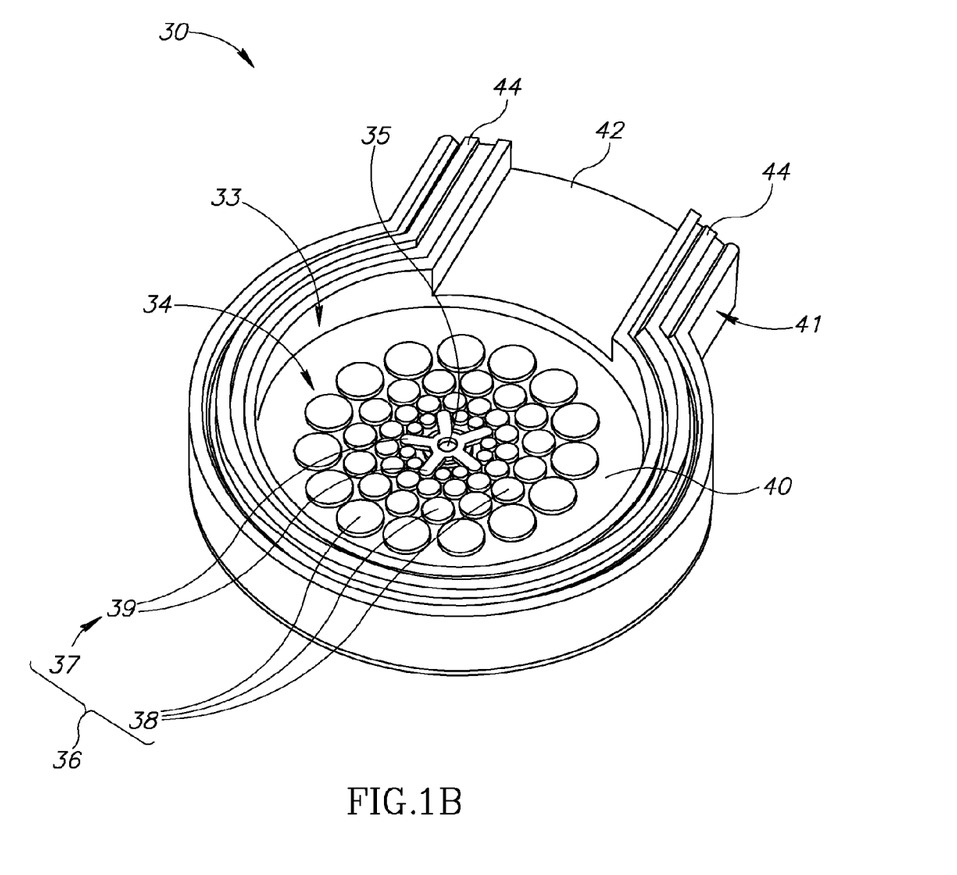
FIG. 1B schematically shows details of a top housing part of the tensiometer shown in FIG. 1A, in accordance with an embodiment of the invention.
Figure 1C:
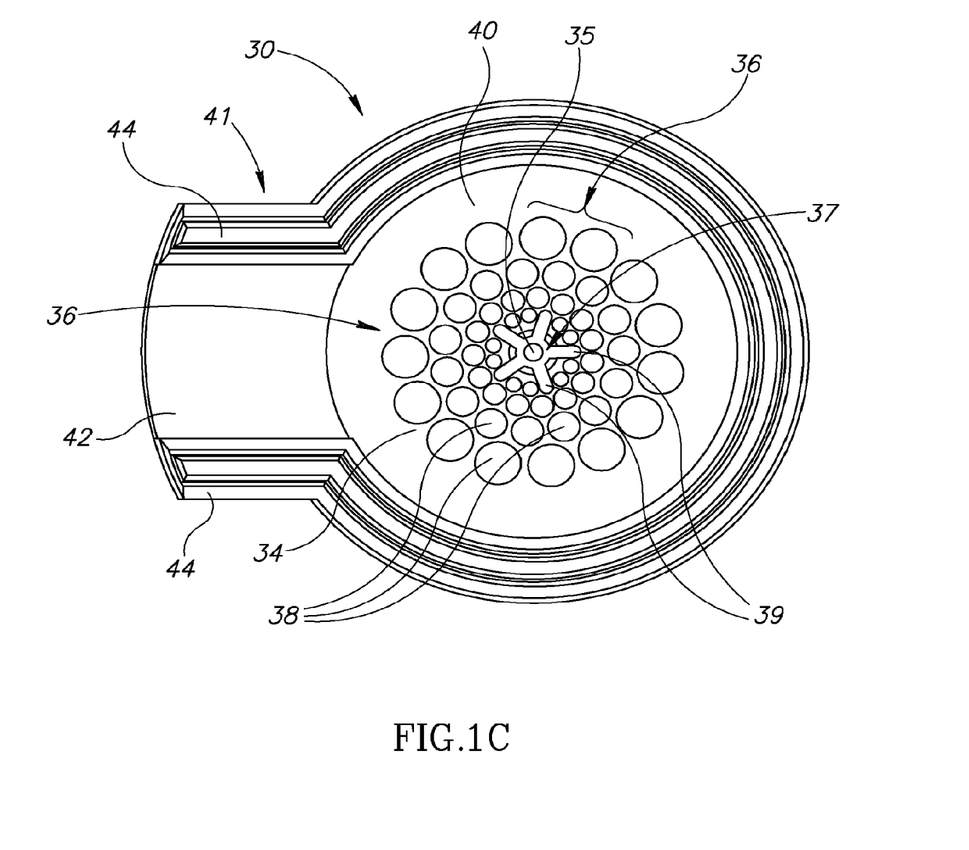
FIG. 1C schematically shows a plan view of the top housing part shown in FIG. 1B, in accordance with an embodiment of the invention.
Figure 1D:
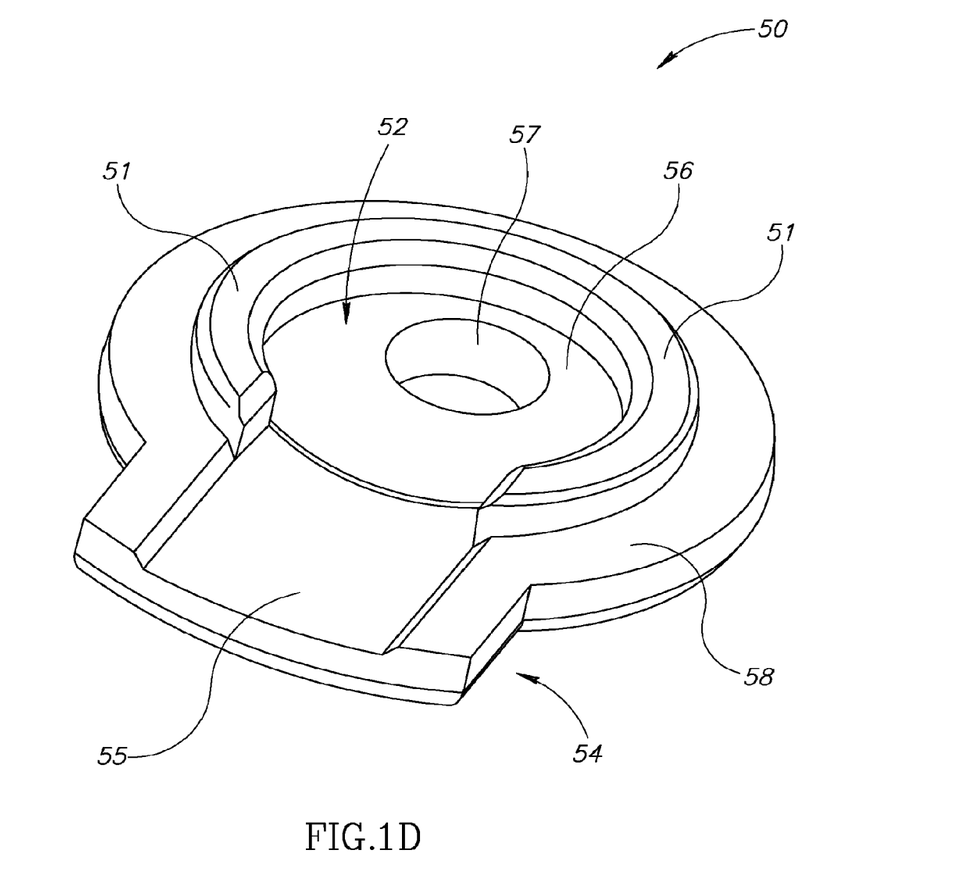
FIG. 1D schematically shows a perspective view of a bottom housing part of the tensiometer shown in FIG. 1A, in accordance with an embodiment of the invention.
Figure 2:
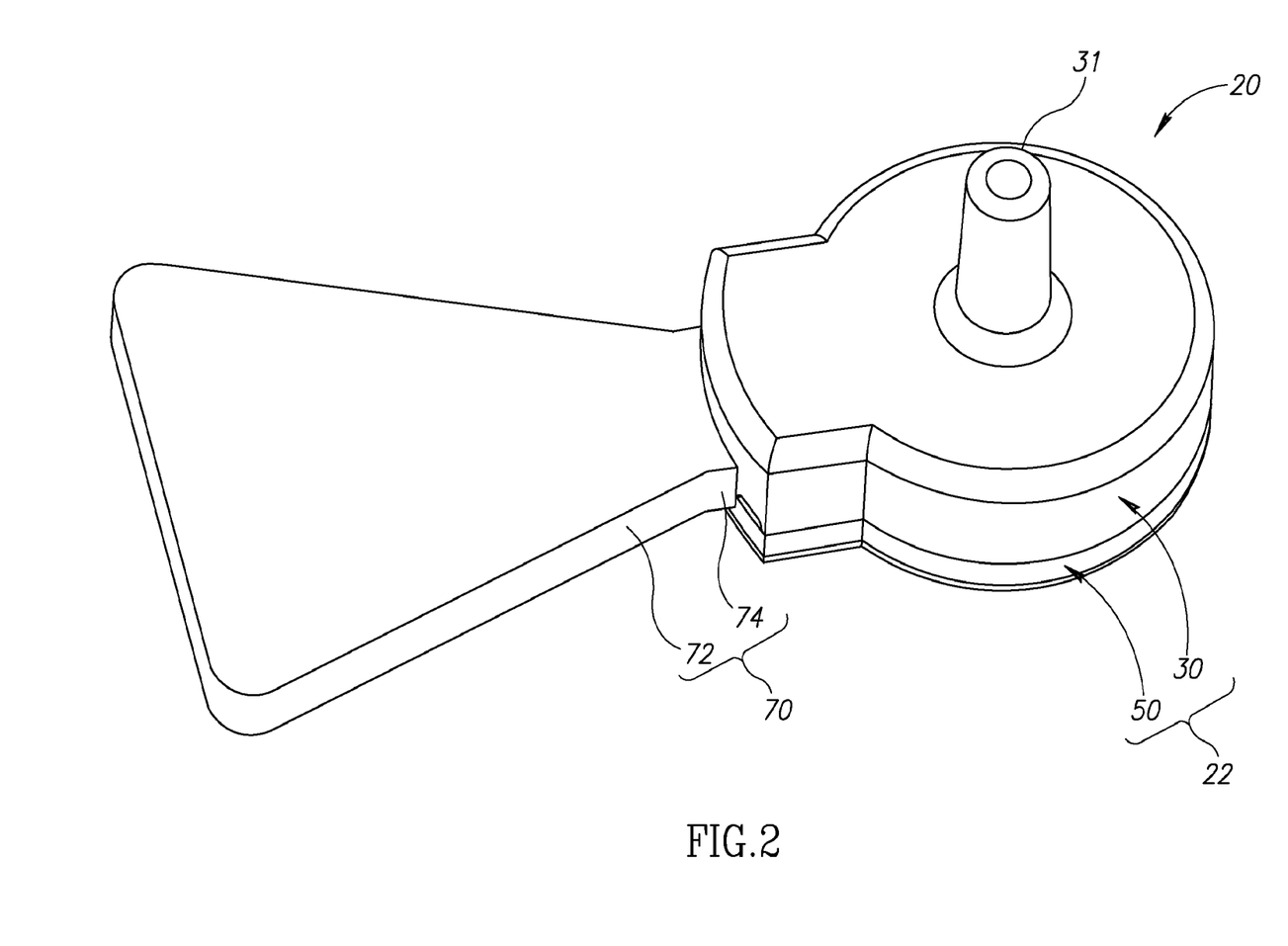
FIG. 2 schematically shows an assembled view of the tensiometer shown in FIGS. 1A-1B, in accordance with an embodiment of the invention.

FIG. 1A schematically shows an exploded view of a tensiometer 20 for measuring water matric potential in a soil, in accordance with an embodiment of the invention. FIGS. 1B-1D schematically show enlarged views of components of tensiometer 20 shown in FIG. 1A. FIG. 2 schematically shows an assembled view of tensiometer 20. For convenience of presentation, apparatus 20 is referred to as a tensiometer, even though, as shown in FIGS. 1A-1D, it optionally, does not comprise a water reservoir and apparatus for providing a measure of pressure in the reservoir.

Tensiometer 20 optionally comprises a housing 22 having first and second housing parts 30 and 50, hereinafter referred to for convenience as housing top 30 and housing bottom 50, a sealing septum 60, a hydraulic soil coupler 70 formed from a porous material and a resilient element 80.

Hydraulic coupler 70 is formed having a soil-coupling region 72 that extends outside of housing 22 when tensiometer 20 is assembled (FIG. 2) and is a part of tensiometer 20 that contacts soil for which the tensiometer provides water matric potential measurements and hydraulically couples the tensiometer to the soil. Optionally soil-coupling region 72 enlarges with distance from tensiometer housing 22. Hydraulic coupler 70 optionally comprises a neck region 74 and an optionally circular reservoir-coupling region 76 that are discussed below and are located inside housing 22. Hydraulic coupler 70 is optionally formed from a flexible porous material and is optionally such that plants that are to be grown in a soil for which tensiometer 20 is to be used to monitor water matric potential can intrude their roots. Optionally, hydraulic coupler 70 is formed from a material comprising a geotextile.

Housing top 30 comprises a tubular stem 31 having a lumen for connecting tensiometer 20 to a sealed tensiometer water reservoir and is formed having a septum recess 33, shown in a perspective view of first housing part 30 from a side opposite that of stem 31 in FIG. 1B, that seats sealing septum 60. A bottom surface 34 of septum recess 33 is formed having an inlet hole 35, clearly shown in a plan view of housing top 30 in FIG. 1C, through which water from a reservoir connected to stem 31 enters tensiometer 20. Bottom surface 34 of septum recess 33 is optionally formed having a water flow labyrinth 36 comprising an entrance, "detour" baffle 37 that covers portions of inlet hole 35 and a plurality of raised cylindrical baffles 38. Detour baffle 37 is optionally "starfish shaped" comprising five angularly, equally spaced arms 39. Labyrinth 36 is surrounded by an annular, optionally planar surface 40 devoid of labyrinth components. Housing top 30 optionally comprises a neck 41 formed having a channel 42 for receiving neck region 74 of hydraulic coupler 70 and optionally comprises an assembly ridge 44 for mounting housing top 30 to housing bottom 50.

Sealing septum 60 optionally comprises a porous septum membrane 61 supported by an annular septum frame 62, which optionally protrudes on either side of the plane of the septum membrane. When tensiometer 20 is assembled, the annular septum frame seats on annular region 40 of bottom surface 34 and septum membrane 61 optionally rests on and is supported by detour and cylindrical baffles 37 and 38.

Septum membrane 61 transmits water but is characterized by a bubbling pressure, hereinafter referred to as an "operating bubbling pressure", when wet that is equal to a maximum water matric potential, typically between about ≤0.2 bar to about −0.7 bar, expected to be encountered in a soil in which tensiometer 20 is to be used. Optionally, the operating bubbling pressure of porous membrane 61 is equal to about 1 atmosphere. As a result, water can pass through membrane 61 relatively easily, but for a pressure differential across the membrane less than or equal to about a maximum water matric potential of soil in which tensiometer 20 is used, membrane 61 is substantially impervious to air. Optionally, membrane 61 is a layered structure, schematically shown in an inset 66 in FIG. 1A, and optionally comprises a porous layer 63, which transmits water but when wet is impervious to air for pressures less than an appropriate operating bubbling pressure, sandwiched between two support layers 64. Optionally, porous layer 63 is formed by way of example from a ceramic, and/or a sintered metal and/or a suitable woven or non-woven fabric having suitable porosity. Support layers 64 are optionally meshed, or screen-like layers formed from any suitably rigid and strong material. Optionally, porous layer 63 is characterized by an average pore size from about 0.5 to about 1 micron. Optionally, support layers are formed from a metal and/or plastic.

Housing bottom 50 is formed to mate with housing top 30 and is optionally formed having a mating ridge 51 that is matched to fit inside recess 33 (FIG. 1B) formed in housing top 30 so that it aligns the housing top and bottom. Mating ridge 51 defines a portion of a boundary of a recess 52 that seats reservoir-coupling region 76 (FIG. 1A) of hydraulic coupler 70. The housing bottom also comprises a neck 54 formed having a channel 55 that matches neck 41 and channel 42 respectively of housing top 30. A bottom surface 56 of recess 52 is optionally formed having a cavity 57 for receiving resilient element 80, optionally in a shape of a sphere, formed from an elastic material. An outer, optionally planar peripheral border 58 surrounds mating ridge 51 and channel 55.

When tensiometer 20 is assembled, assembly ridge 44 of housing top 30 contacts and is bonded to peripheral border 58 of housing bottom 50 and mating ridge 51 presses annular septum frame 62 to annular surface 40 of housing top 30 to secure septum 50 in septum recess 33 of the housing top. Resilient sphere 80 is slightly compressed and urges reservoir-coupling region of hydraulic coupler 70 to resiliently press on septum membrane 61 and the septum membrane to rest securely on water labyrinth baffles 37 and 38. Because of the secure contact between septum membrane 61 and labyrinth baffles 37 and 38, water that enters tensiometer 20 is distributed substantially equally over the surface of septum membrane 61 that contacts the labyrinth baffles. Starfish detour baffle 37 operates to direct substantially equal portions of water that enters inlet hole 35 to flow radially in each of five different sectors defined by the starfish baffle arms 39. Cylindrical baffles 38 disperse radially flowing water azimuthally. As a result, water that enters tensiometer 20 through inlet hole 35 wets substantially equally all regions of septum membrane 61 and the membrane becomes substantially impervious to passage of air for the bubbling pressure for which it is intended.

Figure 3:
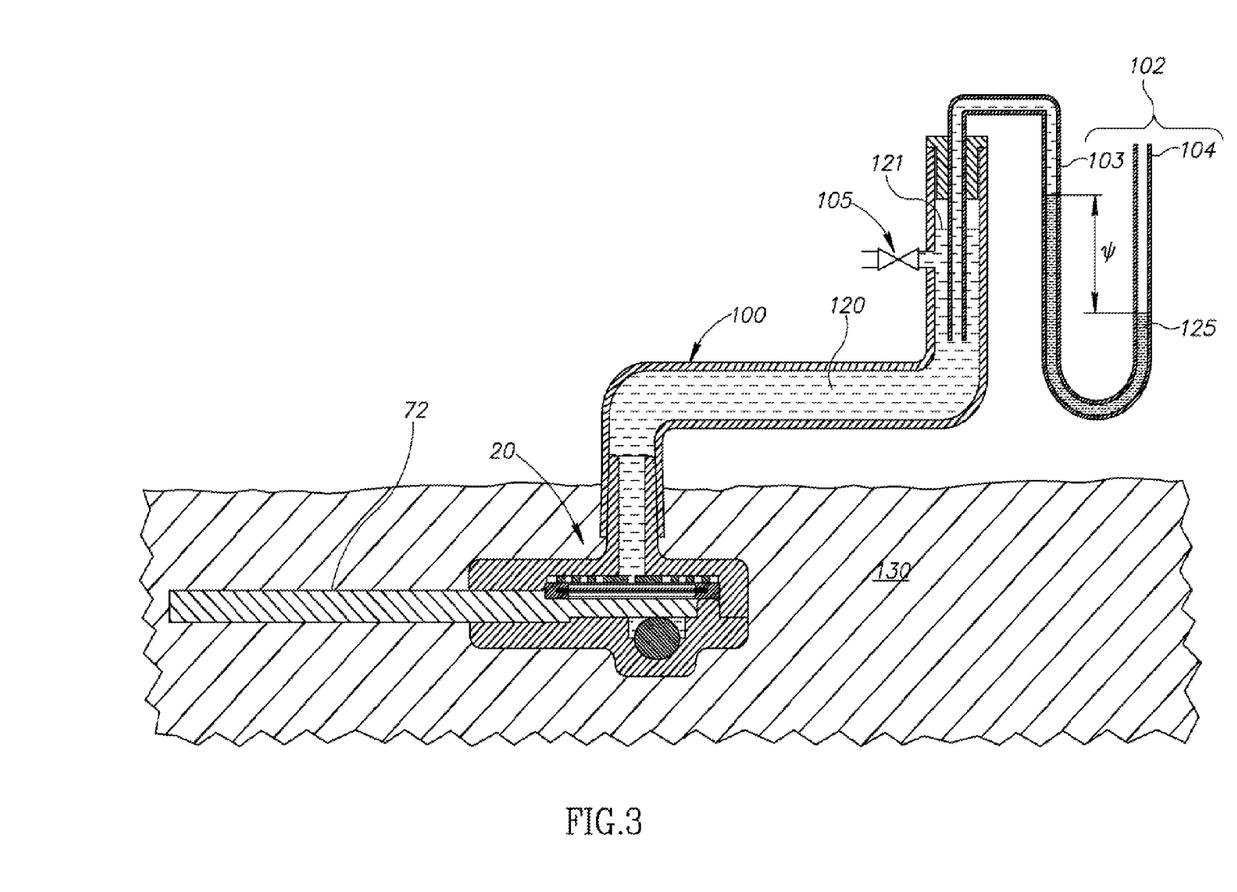
FIG. 3 schematically shows a side cross-sectional view of the tensiometer shown in FIG. 1A and FIG. 2 connected to a sealed water reservoir, in accordance with an embodiment of the invention.

FIG. 3 schematically shows a side cross-sectional view of tensiometer 20 shown in FIG. 1A and FIG. 2 connected to a sealed water reservoir 100 partially filled with water 120 and being used to determine a value for the water matric potential $\psi$ of a soil region 130, in accordance with an embodiment of the invention. It is noted that whereas water reservoir 100 is shown above the surface of soil region 130, in practice, the water reservoir is generally located below the surface of soil for which the tensiometer is used to measure water matric potential.

Tensiometer 20 is positioned in soil region 130 so that soil-coupling region 72 of hydraulic coupler 70 is in contact with soil in the soil region. A pressure gauge 102 is coupled to water reservoir 100 to measure pressure in the reservoir. In FIG. 3, by way of example, the pressure gauge is shown as a manometer having a left hand branch 103 coupled to water reservoir 100 and a right hand branch 104 exposed to atmospheric pressure. The manometer is assumed to comprise mercury 125 as a manometer fluid, and left hand branch 103 between the mercury and water 120 in reservoir 100 is filled with water. Whereas in FIG. 3 pressure gauge 102 is shown as a manometer, in practice any suitable pressure gauge or sensor known in the art may be used to provide a measure of pressure in reservoir 100.

Hydraulic coupler 70 provides a hydraulic coupling between soil in soil region 130 and water in water reservoir 100 via contact between reservoir-coupling region 76 (FIG. 1A) of the hydraulic coupler and sealing septum 60. The soil draws water from or introduces water into water reservoir 100 via the hydraulic coupler depending on whether the water matric potential of soil region 130 is greater than or less than the pressure in water reservoir 100. Equilibrium is established for which there is substantially no water flow from or into the reservoir when pressure in the reservoir is equal to the soil water matric potential. Since the matric potential is almost always negative, there is a vacuum in reservoir 100 above a waterline 121 of water 120 in the reservoir. In FIG. 3 mercury 125, is higher in left hand branch 103 of the manometer connected to water reservoir 100 than in right hand branch 104 of the manometer exposed to atmospheric pressure. A difference between the height of mercury in the left and right hand branches provides a measure of the partial vacuum in water reservoir 100 and thereby of the matric potential $\psi$.

In order to operate reliably, advantageously, septum membrane is maintained properly wetted and does not have air trapped in its pores. However, during operation, air might leak through hydraulic coupler 70 or seep through water 120 and be trapped by the membrane or in spaces between baffles 37 and 38 of labyrinth 39. In order to purge septum 61 and/or labyrinth 36 of air that they may trap, a purge valve 105 is optionally connected to reservoir 100. Purge valve 105 is connected to a suitable source of water (not shown) and in accordance with an embodiment of the invention is periodically opened to flush water from the water source through the reservoir, septum membrane 61, and labyrinth 36 to purge the septum and labyrinth of air they may have trapped. Advantageously, the space above waterline 121 is substantially a vacuum and water provided via purge valve 105 is used to remove air from reservoir 100. Thus, as seen in FIG. 3, the tensiometer 20 is connected to the water source via the sealed water reservoir 100; and the purge valve 105 is adapted to connect the water source to the sealed water reservoir 100 at a point below the waterline 121 of the sealed water reservoir 100.

In an embodiment of the invention, to provide a measure of matric potential $\psi$ in a region of a field, a plurality of tensiometers, optionally of a type shown in FIGS. 1A-3, is positioned in soil at different locations in the field and coupled to a common sealed water reservoir. Pressure in the common water reservoir provides a measure, i.e. "representative matric potential", of water matric potential in the field that is intermediate a highest and lowest value for water matric potential provided by the tensiometers. Optionally, the field is an agricultural field for growing plants and the plurality of tensiometers and representative matric potential is used to control irrigation of the plants in the field.

Figure 4:
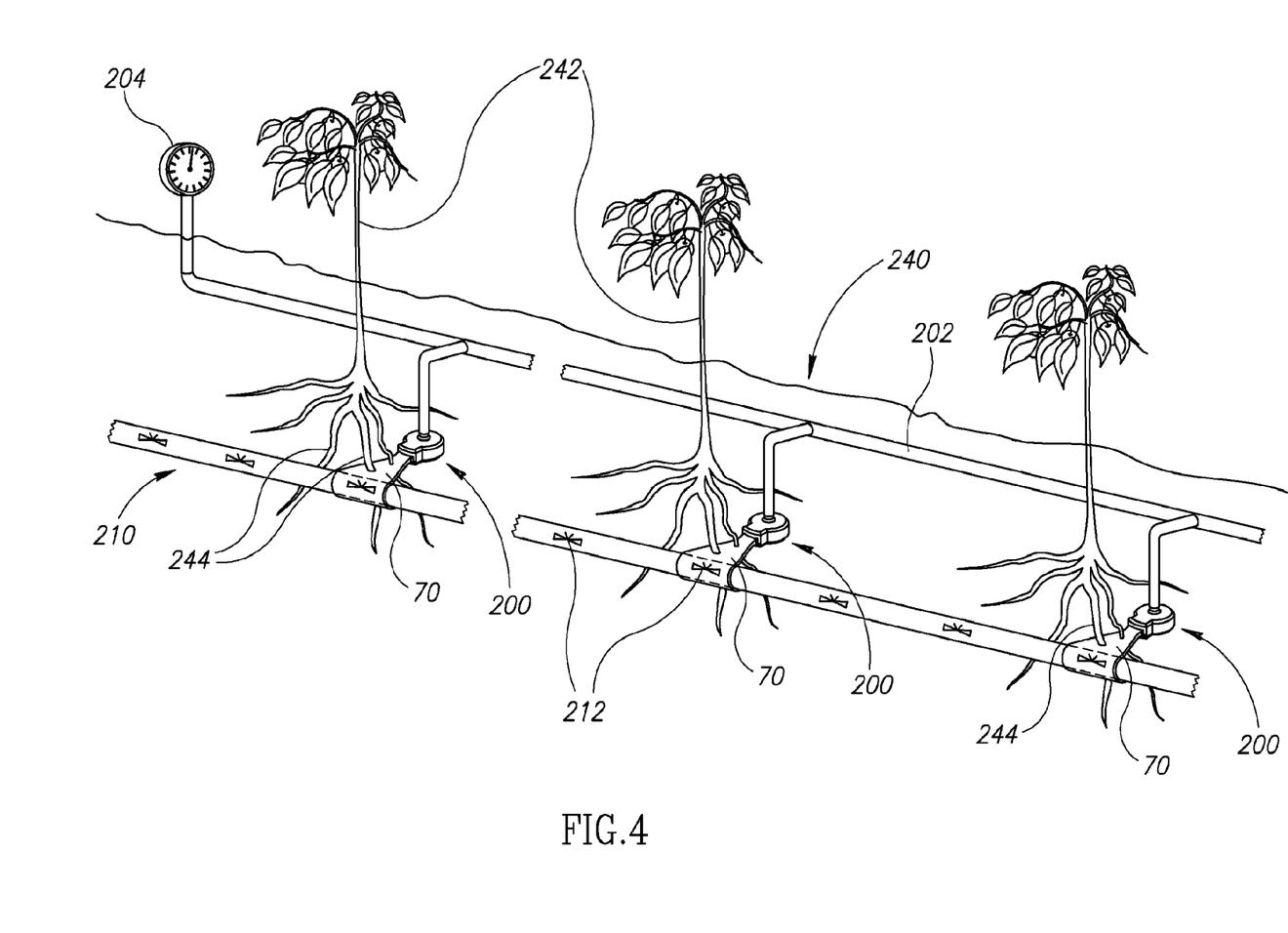
FIG. 4 schematically shows a configuration of tensiometers distributed in the soil of an agricultural field in which plants are grown, in accordance with an embodiment of the invention.

FIG. 4 schematically shows a configuration of tensiometers 200 distributed in the soil of an agricultural field 240 in which plants 242 are grown, in accordance with an embodiment of the invention. The tensiometers are connected to a same water reservoir 202 connected to a pressure gauge 204 used to provide a measure of a partial vacuum in the reservoir and thereby of a representative matric potential of the region of agricultural field 240 in which the tensiometers are located.

By way of example, in FIG. 4 plants 242 are irrigated using an irrigation pipe 210, comprising integrated emitters 212 and tensiometers 200 are of a type shown in FIGS. 1A-3 having hydraulic couplers 70 formed from a geotextile in which roots 244 of plants 242 are able to grow. In accordance with an embodiment of the invention, each tensiometer 200 coupled to water reservoir 202 is located in a neighborhood of a plant 242 and has its hydraulic coupler 70 wrapped around a region of irrigation pipe 210 in which an emitter 212 is located. Some roots 244 of plants 242 are shown growing into the geotextile fabric of hydraulic couplers 70 of tensiometers 200. Because of the close proximity of emitters 212 and plant roots 244 to hydraulic couplers 70, each tensiometer 200 is responsive to soil water matric potential to which plants 242 are relatively sensitive and to changes in the matric potential produced by water emitted by emitters 212.

In an embodiment of the invention, measurements of changes in pressure in reservoir 202, and thereby of changes in representative water matric potential of field 240, provided by pressure gauge 204 are used to control water emitted by emitters 212. When the representative water matric potential provided by pressure gauge 204 falls below a desired lower threshold for water matric potential, emitters 212 are controlled to release water to the soil. When the representative water matric potential rises above a desired upper threshold, the emitters are prevented from delivering water to the soil.

Optionally, emitters 212 release water to soil region 240 only after pressure in irrigation pipe 210 rises above a release water threshold pressure and water released by emitters 212 is controlled by controlling pressure in the irrigation pipe. In some embodiments of the invention, water release is controlled by pulsing pressure in irrigation pipe 210 above the emitter threshold pressure. In some embodiments of the invention, pressure pulses are periodic and are characterized by a pulse length. The period and pulse length of the pressure pulse are optionally determined responsive to a "hydration" relaxation time of soil in soil region 240 characteristic of a time it takes the soil to reach a limiting water matric potential following release of a quantity of water to the soil by an emitter 212 during a pressure pulse. Controlling release of water in accordance with an embodiment of the invention by pulsing water pressure responsive to a soil hydration relaxation time can be advantageous in providing relatively accurate control of irrigation. For example, it can be advantageous in preventing over irrigation of plants 242.

The inventors of embodiments of the invention have carried out irrigation experiments in which plants were irrigated responsive to a representative matric potential in accordance with an embodiment of the invention. The inventors found that they were able to achieve relatively improved crop yields with relatively smaller quantities of water than would normally be provided to the plants.

Under some conditions, a representative water matric potential provided by a plurality of tensiometers in accordance with an embodiment of the invention is substantially equal to an average of the measurements provided by the tensiometers. For example, assume that at a location of an "i-th" tensiometer 200, for convenience represented by "$T_i$", in soil region 240, the water matric potential is $\psi_i$. At equilibrium, a partial vacuum in water reservoir 202 settles down to a pressure equal to that of a representative matric potential "$\psi_o$". At the representative matric potential, as much water enters water reservoir 202 from tensiometers $T_i$ at locations for which matric potentials $\psi_i > \psi_o$ as exits the water reservoir from tensiometers $T_i$ at locations for which $\psi_i < \psi_o$. Assume that water flow into or out of a tensiometer $T_i$ is proportional to $(\psi_i - \psi_o)/R$ where R is a resistance to water transport of soil in soil region 240, which is the same for all locations of tensiometers $T_i$, and is independent of $(\psi_i - \psi_o)$. Then at equilibrium, $$\sum_i^N \frac{(\psi_i - \psi_o)}{R} = 0 \text{ and } \psi_o = \left(\frac{1}{N}\right)\sum_i^N \psi_i$$

so that $\psi_o$ is an average of all the $\psi_i$. However, it is expected that, in general, R will not only not be the same for all locations of soil region 130 but will be dependent on $(\psi_i - \psi_o)$. As a result, it is expected that a given representative water matric potential will in general be some sort of weighted average of the matric potential at the locations of each of tensiometers 200.

Figure 5A:
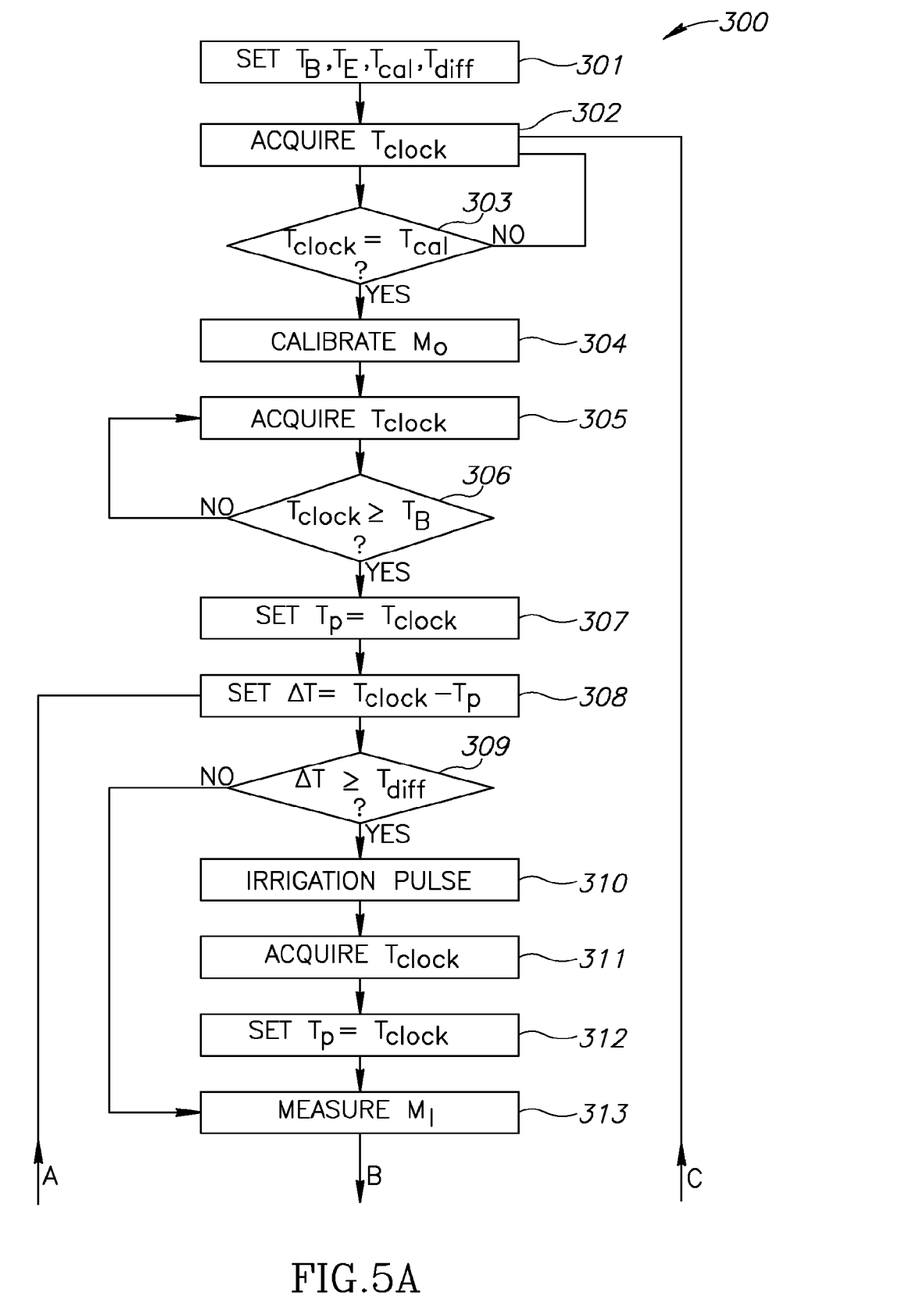
FIGS. 5A and 5B show a flow diagram of an algorithm for controlling irrigation of a field responsive to water matric potential in accordance with an embodiment of the invention.
Figure 5B:
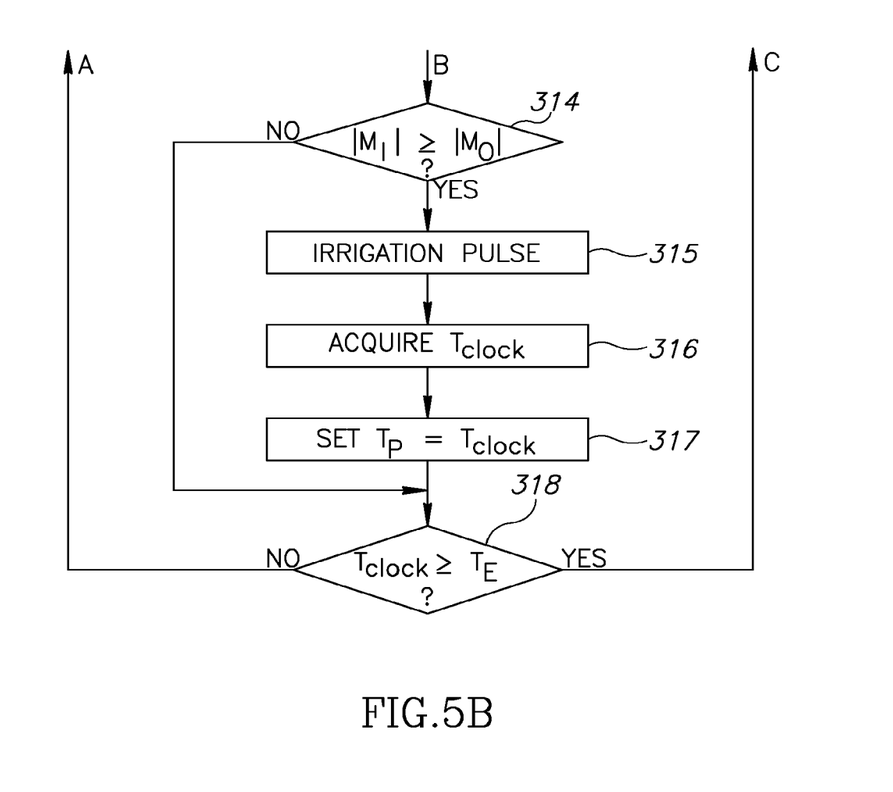

In some embodiments of the invention, provision of water to an agricultural field by an irrigation system, such as agricultural field 240 and the irrigation system shown in FIG. 4, which provides measurements of soil water matric potential $\psi$ is controlled in accordance with an algorithm 300 having a flow diagram similar to that shown in FIGS. 5A and 5B. The flow diagram delineates an optionally diurnal water provision cycle in which the irrigation system provides pulses of water to the field subject to certain "trigger" conditions, described below, prevailing.

In a block 301, optionally values for parameters that control the water provision cycle $T_{cal}$, $T_{diff}$, $T_B$ and $T_E$ are determined. $T_{cal}$ is a time during the diurnal cycle at which the irrigation system calibrates water matric potential measurements and acquires a calibration water matric potential measurement $M_o$. $M_o$ is optionally acquired during night after a period of time during which irrigation was not provided and water demand by plants in the field is minimal. Optionally, $T_{cal}$ is about 0500. $T_{diff}$ is an optionally fixed, maximum time lapse allowed by algorithm 300 between provision of pulses of water to field 240. Optionally, $T_{diff}$ is equal to about 5 hours. $T_B$ is a time following time $T_{cal}$ at which the irrigation system begins a period of "active irrigation" in which it provides a pulse of water to field 240 when a trigger condition occurs. $T_E$ is a time at which the active irrigation period ends. Optionally, $T_B$ is about an hour later than $T_{cal}$ and $T_E$ is a time at about dusk, for example about 1700.

In a step 302, algorithm 300 checks a system clock (not shown) to acquire a reading of the time, "$T_{clock}$". In a decision block 303 the time $T_{clock}$ is checked to see if it is about equal to $T_{cal}$. If it is not, then the algorithm returns to block 302 to acquire a new reading for $T_{clock}$. If on the other hand $T_{clock}$ is about equal to $T_{cal}$, algorithm 300 advances to a block 304 and acquires a calibration reading, $M_o$, of the soil matric potential $\psi$. The algorithm then proceeds to acquire another reading, $T_{clock}$, of the system clock in a block 305 and then proceeds to a decision block 306. In decision block 306 algorithm 300 determines if $T_{clock}$ is greater than or equal to time $T_B$ at which active irrigation of field 240 is to commence. If $T_{clock}$ is less than $T_B$, the algorithm returns to block 305 to acquire another reading for $T_{clock}$. If on the other hand $T_{clock}$ is greater than or about equal to $T_B$, algorithm 300 advances to a block 307 and sets a variable time parameter $T_P$ equal to $T_{clock}$, and in a block 308 optionally sets $\Delta T$ equal to $(T_{clock} - T_P)$, which initializes $\Delta T$ to zero.

Optionally, in a decision block 309, algorithm 300 determines if $\Delta T$ is greater than $T_{diff}$. If it is not, (which at this stage, immediately after initialization, is the case) algorithm 300 optionally skips to a block 313. In block 313 algorithm 300 acquires a measurement $M_I$ of the water matric potential of field 240, optionally responsive to readings from tensiometers 200 (FIG. 4), and proceeds to determine in a decision block 314 if the absolute value of $|M_I|$ is greater than the absolute value $|M_o|$ acquired in block 304. If $|M_I|$ is greater than $|M_o|$, algorithm 300 optionally proceeds to a block 315 and controls the irrigation system to provide a pulse of water to field 240.

In some embodiments of the invention, a pulse of water provided by the irrigation system is determined to provide about 0.6 liters of water per m² of field 240. The inventors have determined that aforementioned amount of water per pulse is convenient to maintain appropriate irrigation, generally, if a time between pulses is greater than or about equal to 0.5 hours. In some embodiments of the invention, algorithm 300 increases an amount of water provided by an irrigation pulse if time between pulses decreases to less than about 0.5 hours. For example, if irrigation algorithm 300 "finds" that $|M_I|$ increases relatively rapidly, indicating a requirement for irrigation pulses every 0.25 hours, optionally the algorithm increases the mount of water provided by an irrigation pulse. Optionally, the algorithm increases water provided by a pulse to about 0.9 liters/m² if it finds that demand for irrigation pulses reaches a rate of about 4 pulses per hour.

Following provision of the pulse of water, algorithm 300 proceeds to a block 316 and acquires a new reading for $T_{clock}$ and resets $T_P$ to $T_{clock}$ in a block 317. It is noted that in decision block 314, if $|M_I|$ is less than $|M_o|$, algorithm 300 skips blocks 315 to 317, does not provide a pulse of water, and goes directly to a decision block 318 shown in FIG. 5B.

Returning to block 309 if $\Delta T$ is greater than $T_{diff}$ algorithm 300 does not skip to block 314 where it measures $M_I$, but rather, optionally, proceeds to a block 310 and provides a pulse of irrigating water to field 240. Thereafter the algorithm proceeds to a block 311, acquires a new reading for $T_{clock}$, and in a block 312 resets $T_P$ to $T_{clock}$. It proceeds to block 314 to measure $M_I$ and via blocks 315-317 eventually to decision block 318.

In decision block 318 algorithm 300 determines if $T_{clock}$ is greater than or equal to $T_E$, the time set in block 301 at which the active irrigation period ends and a new irrigation cycle begins. If $T_{clock}$ is less than $T_E$, algorithm 300 returns to block 308 and resets $\Delta T$, otherwise, the algorithm returns to block 302 to begin the cycle again.

Figure 6:
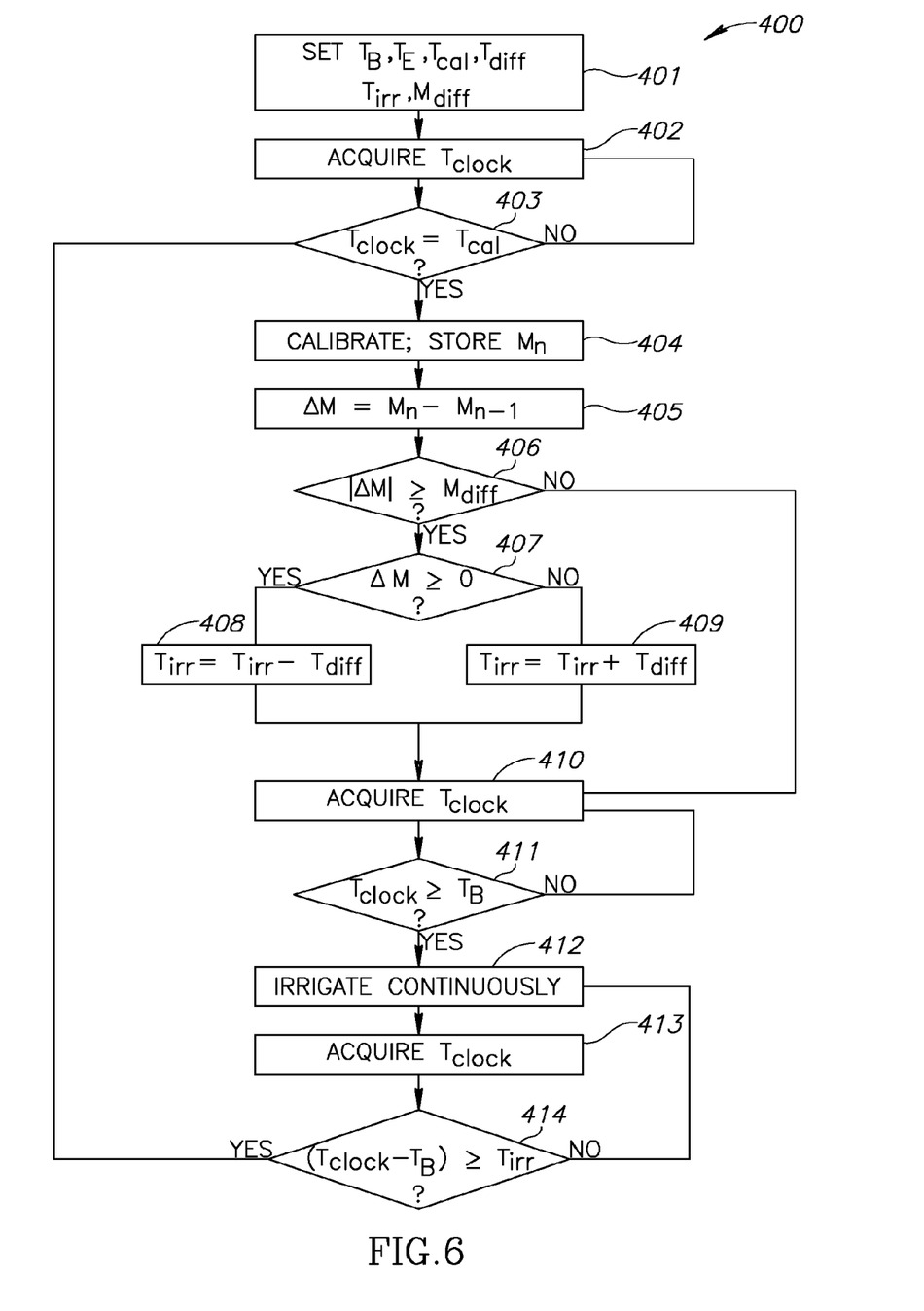
FIG. 6 shows a flow diagram of another algorithm for controlling irrigation of a field responsive to water matric potential in accordance with an embodiment of the invention.

In some embodiments of the invention, an agricultural field, such as field 240 (FIG. 4) is irrigated in accordance with an algorithm 400 having a flow diagram shown in FIG. 6. Algorithm 400 controls an irrigation system to continuously provide water to agricultural field 240 during an active irrigation period instead of by pulsing water provision.

In a block 401 of algorithm 400, optionally parameters $T_B$, $T_E$, $T_{diff}$, $T_{irr}$, $T_{cal}$, and $M_{diff}$ are set. As in algorithm 300, $T_B$ and $T_E$ are begin and end times of active irrigation and $T_{cal}$ is a calibration time. $T_{irr}$ is an initial value for duration of the active irrigation period, and $T_{diff}$ is an adjustment to $T_{irr}$, which algorithm 400 makes subject to certain water matric potential conditions of field 240. $M_{diff}$ is an optionally fixed, maximum change in water matric potential for which algorithm 400 does not adjust $T_{irr}$. Affects of the parameters set in block 401 on decisions of algorithm 400 are clarified below. In some embodiments of the invention, $T_{irr}$ and $L_{diff}$ have values equal to about 3 hours and 0.2 hours, respectively. $M_{diff}$ is optionally a positive number having value equal to a fraction less than one of a typical matric potential for the field being irrigated with the irrigation system. Optionally, $M_{diff}$ is equal to about 5% of a calibration matric potential acquired for the field. Optionally, for a given day, $M_{diff}$ is equal to 5% of a calibration matric potential for a previous day.

In a block 402, algorithm 400 acquires a value for $T_{clock}$, and optionally in a decision block 403 determines if $T_{clock}$ is equal to $T_{cal}$. If it is not it returns to block 402 to acquire a new value for $T_{clock}$. On the other hand, if $T_{clock}$ is equal to $T_{cal}$ the algorithm proceeds to a block 404 and acquires a reading "$M_n$" for the water matric potential $\psi$ of field 240. The subscript "n" refers to an "n-th" day, assumed a current day, of operation of the irrigation system in providing water to field 240. In a block 404, algorithm 400 stores the value for $M_n$ in a suitable memory. In a block 405 the algorithm optionally assigns a value to $\Delta M$ equal to a difference between of the current reading $M_n$ of the water matric potential and a value of a reading, $M_{n-1}$, of the water matric potential acquired for the day before the current day.

In a decision block 406, algorithm 400 determines if an absolute value of $\Delta M$ is greater than or equal to $M_{diff}$. If it is, the algorithm proceeds to a decision block 407 to determine if $\Delta M$ is greater than or equal to zero. If $\Delta M$ is greater than zero, the algorithm proceeds from block 407 to a block 408 where it decreases $T_{irr}$ by an amount $T_{diff}$ and then proceeds to a block 410 to acquire time $T_{clock}$. If $\Delta M$ is less than zero, the algorithm proceeds from block 407 to a block 409 where it increases $T_{irr}$ by an amount $T_{diff}$ and then proceeds to a block 410 to acquire time $T_{clock}$.

If in decision block 406 the absolute value of $\Delta M$ is less than $M_{diff}$, then algorithm 400 skips directly from block 406 to block 410 to acquire $T_{clock}$, skipping blocks 407, 408 and 409.

From block 410, the algorithm proceeds to decision block 411. In decision block 411, algorithm 400 determines if $T_{clock}$ acquired in block 410 is greater than or equal to the active irrigation begin time $T_B$. If it is not, it returns to block 410 to acquire a new value for $T_{clock}$ and then to block 411 to test the new $T_{clock}$. If in block 411 the algorithm determines that $T_{clock}$ is greater than or equal to $T_B$, the algorithm proceeds to a block 412 and begins continuous irrigation of field 240.

From block 412 the algorithm continues to a block 413 to acquire a new value for $T_{clock}$ and in a decision block 414 determines if $(T_{clock}-T_B)$ is greater than or equal to $T_{irr}$. If it is not, the algorithm returns to block 412 to continue continuous irrigation of field 240. If on the other hand, $(T_{clock}-T_B) > T_{irr}$ then the algorithm ends continuous irrigation and returns to block 403.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

The invention has been described with reference to embodiments thereof that are provided by way of example and are not intended to limit the scope of the invention. The described embodiments comprise different features, not all of which are required in all embodiments of the invention. Some embodiments of the invention utilize only some of the features or possible combinations of the features. Variations of embodiments of the described invention and embodiments of the invention comprising different combinations of features than those noted in the described embodiments will occur to persons of the art. The scope of the invention is limited only by the following claims.

Although the present embodiment has been described to a certain degree of particularity, it should be understood that various alterations and modifications could be made without departing from the scope of the disclosure as hereinafter claimed.

What is claimed is:

1. A tensiometer for use in determining matric potential of a soil comprising:
   a water inlet;
   a hydraulic coupler comprising a porous material for providing hydraulic coupling between water that enters the inlet and the soil;
   a septum that seals water that enters the inlet against ingress of air via the porous material; and
   a valve adapted to connect the tensiometer to a water source and operable to enable water from the water source to enter the tensiometer and flush the hydraulic coupler.

2. A tensiometer according to claim 1 wherein the porous material is adapted to enable growth of plant roots therein.

3. The tensiometer according to claim 1, wherein:
   the tensiometer is connected to the water source via a reservoir; and
   the valve is adapted to connect the water source to the reservoir at a point below a waterline of the reservoir.

4. The tensiometer according to claim 1, wherein:
   the tensiometer is connected to the water source via a reservoir; and
   the valve is operable to enable water from the water source to enter the reservoir and remove air therefrom.

5. Apparatus for use in determining matric potential of a soil comprising:
   a plurality of tensiometers in accordance with claim 1; and
   a same water reservoir to which said plurality of tensiometers are hydraulically coupled.

6. An irrigation system comprising:
   an irrigation pipe having at least one output orifice for outputting water from the pipe; and
   a plurality of tensiometers in accordance with claim 1 connected to the irrigation pipe.

7. The irrigation system according to claim 6, wherein:
   the irrigation pipe comprises a plurality of integrated emitters, each emitter having an output orifice.

8. The irrigation system according to claim 6, wherein:
   each of said plurality of tensiometers is connected to a common water reservoir.

9. The irrigation system according to claim 8, wherein:
   the water reservoir comprises a device for providing a measure of pressure in the water reservoir.

10. A tensiometer according to claim 1 wherein:
    the tensiometer comprises a housing; and
    the hydraulic coupler comprises:
       a reservoir-coupling region located inside the housing; and
       a soil-coupling region that extends outside of the housing to hydraulically couple the tensiometer to soil.

11. A tensiometer according to claim 10 wherein:
    the housing comprises a housing top and a housing bottom; and
    the soil-coupling region extends outside of the housing, between the housing top and housing bottom.

12. A tensiometer according to claim 10 wherein:
    the housing comprises a housing top and a housing bottom; and
    a bottom surface of the housing top is provided with a water flow labyrinth comprising a plurality of baffles configured to disperse water entering the tensiometer.

13. A tensiometer for use in determining matric potential of a soil comprising:
    a water inlet;
    a hydraulic coupler comprising a porous material for providing hydraulic coupling between water that enters the inlet and the soil;
    a valve adapted to connect the tensiometer to a water source and operable to enable water from the water source to enter the tensiometer and flush the hydraulic coupler; and
    a septum that seals water that enters the inlet against ingress of air via the porous material; wherein:
    the septum comprises a septum surface, at least a part of which is contiguous with water that enters the water inlet.

14. A tensiometer according to claim 13 wherein the tensiometer comprises a water labyrinth having baffles.

15. A tensiometer according to claim 14 wherein a portion of the septum surface contacts the baffles.

16. A tensiometer according to claim 15 wherein the septum comprises a membrane and the septum surface is a surface of the membrane.

17. A tensiometer according to claim 16 wherein the membrane comprises a plurality of layers.

18. A tensiometer according to claim 17 wherein the layers comprise a first layer having a bubbling pressure greater than about a maximum absolute value of the matric potential of the soil in which the tensiometer is used.

19. A tensiometer according to claim 18 wherein the bubbling pressure is about equal to one atmosphere.

20. A tensiometer according to claim 18 wherein the first layer is supported by at least one support layer.

21. A tensiometer according to claim 20 wherein the first layer is sandwiched between two support layers.

22. Apparatus for use in determining matric potential of a soil comprising:
    a tensiometer comprising:
       a housing comprising a housing top and a housing bottom;
       a water inlet; and
       a hydraulic coupler comprising:
          a porous material for providing hydraulic coupling between water that enters the inlet and the soil; and
          a soil-coupling region extending outside of the housing, between the housing top and housing bottom; and
    a valve adapted to connect the tensiometer to a water source and operable to enable water from the water source to enter the tensiometer and flush the hydraulic coupler.

23. An apparatus according to claim 22 wherein:
    the hydraulic coupler further comprises:
       a reservoir-coupling region located inside the housing.

24. An apparatus according to claim 22, wherein:
    the tensiometer is connected to the water source via a reservoir; and
    the valve is adapted to connect the water source to the reservoir at a point below a waterline of the reservoir.

25. An apparatus according to claim 22, wherein:
    the tensiometer is connected to the water source via a reservoir; and
    the valve is operable to enable water from the water source to enter the reservoir and remove air therefrom.

26. Apparatus for use in determining matric potential of a soil comprising:
    a tensiometer comprising:
       a housing comprising a housing top and a housing bottom;
       a water inlet; and
       a hydraulic coupler comprising:
          a porous material for providing hydraulic coupling between water that enters the inlet and the soil; and a valve adapted to connect the tensiometer to a water source and operable to enable water from the water source to enter the tensiometer and flush the hydraulic coupler; wherein:

a bottom surface of the housing top is provided with a water flow labyrinth comprising a plurality of baffles configured to disperse water entering the tensiometer.

27. An apparatus according to claim 26 wherein:
the hydraulic coupler further comprises:
a reservoir-coupling region located inside the housing.

28. A tensiometer for use in determining matric potential of a soil comprising:
a water inlet;
a hydraulic coupler comprising a porous material for providing hydraulic coupling between water that enters the inlet and the soil;
a valve adapted to connect the tensiometer to a water source and operable to enable water from the water source to enter the tensiometer and flush the hydraulic coupler; and
a septum that seals water that enters the inlet against ingress of air via the porous material; wherein:
the septum has a bubbling pressure greater than about a maximum absolute value of the matric potential of the soil in which the tensiometer is used.

29. A tensiometer for use in determining matric potential of a soil comprising:
a water inlet;
a hydraulic coupler comprising a porous material for providing hydraulic coupling between water that enters the inlet and the soil;
a valve adapted to connect the tensiometer to a water source and operable to enable water from the water source to enter the tensiometer and flush the hydraulic coupler;
a septum that seals water that enters the inlet against ingress of air via the porous material; and
an elastic member that resiliently presses the porous material to the septum.

* * * * *